United States Patent [19]

Jain

[11] 4,321,192
[45] Mar. 23, 1982

[54] FRACTIONATION OF PROTEIN MIXTURES BY SALT ADDITION FOLLOWED BY DIALYSIS TREATMENT

[75] Inventor: Surendar M. Jain, Watertown, Mass.

[73] Assignee: Ionics Incorporated, Watertown, Mass.

[21] Appl. No.: 197,441

[22] Filed: Oct. 16, 1980

Related U.S. Application Data

[63] Continuation-in-part of Ser. No. 111,144, Jan. 10, 1980, Pat. No. 4,276,140.

[51] Int. Cl.³ .................. A23J 1/06; A61K 37/04
[52] U.S. Cl. .................. 260/122; 260/112 R; 260/112 B; 424/101; 424/177; 23/902; 128/214 B; 128/DIG. 22; 210/645; 210/646; 210/647; 210/648
[58] Field of Search .............. 204/180 R, 180 P; 260/112 R, 112 B, 121, 122; 424/12, 36, 177, 96, 101; 23/902, 913, 915, 230 B; 128/214 B, DIG. 22; 210/646, 645, 647, 648

[56] References Cited

U.S. PATENT DOCUMENTS

| | | | |
|---|---|---|---|
| 1,600,161 | 9/1926 | Bell .................. | 260/122 |
| 2,461,505 | 2/1949 | Daniel .................. | 424/177 X |
| 2,692,854 | 10/1954 | Henley .................. | 210/645 X |
| 2,726,235 | 12/1955 | Rane et al. .................. | 260/112 B |
| 2,790,790 | 4/1957 | Klostergaard .................. | 260/122 X |
| 3,038,838 | 6/1962 | Spicer et al. .................. | 424/117 |
| 3,203,865 | 8/1965 | Koehler et al. .................. | 210/645 X |
| 3,429,867 | 2/1969 | Bozicevich .................. | 260/122 X |
| 3,706,631 | 12/1972 | Falk .................. | 260/112 B X |
| 3,743,480 | 7/1973 | Falk .................. | 260/112 B X |
| 3,757,005 | 9/1973 | Kautz et al. .................. | 260/122 |
| 3,926,797 | 12/1975 | Gigou et al. .................. | 210/648 X |
| 4,136,094 | 1/1979 | Condie .................. | 260/122 |
| 4,216,205 | 8/1980 | Radowitz .................. | 260/112 B X |
| 4,264,589 | 4/1981 | Felts et al. .................. | 424/177 X |

*Primary Examiner*—Arthur C. Prescott
*Attorney, Agent, or Firm*—Norman E. Saliba

[57] ABSTRACT

A process is described for the fractionation of solutions of protein mixtures which includes the steps of subjecting such solutions to "salting-out", separation of the resulting turbidity, subsequent removal of the "salting-out" agent from the supernatant by dialysis and finally making up the original salt level of the liquid if required. Such a process may be used in therapeutic plasma exchange where removal of immunoglobulins or their complexes therefrom is desired so that the remaining albumin void of immunoglobulins can be administered back to the patient.

1 Claim, 3 Drawing Figures

FRACTIONATION OF PROTEIN MIXTURES BY SALT ADDITION FOLLOWED BY DIALYSIS TREATMENT

This application is a continuation-in-part of parent application Ser. No. 111,144 filed Jan. 10, 1980 now U.S. Pat. No. 4,276,140.

BACKGROUND OF THE INVENTION

Biological fluids such as blood plasma or serum, milk whey, urine, etc. contain a mixture of several proteins. For example, blood plasma contains albumin (3.5–4.5 g/100 ml, M. wt 66,000), fibrinogen (0.20–0.45 g/100 ml, M. wt 340,000), α-globulins (0.4–1.0 g/100 ml) β-globulins (0.8–1.8 g/100 ml, M. wt 160,000), IgM (0.06–0.25 g/100 ml, M. wt. 950,000), etc. (Frank W. Putnam, The Trace Components of Plasma, An Overview). The immunoglobulins (Ig's) are very important since they are involved in the protective and defensive mechanisms against infectious organisms. Clinical diseases characterized by imbalances of these systems of proteins for example either in the ability to recognize invading organisms or to recognize indigenous protein or polynucleic acids, have promoted the basic understanding of the clinical aspects of the science of immunity. Abnormal immunological reactions are now known to cause a wide spectrum of diseases. Examples of diseases known to be associated with immune complex reactions include, for example, serum sickness, flomerulonephritis and myasthenia gravis. Plasmapheresis is a technique used to curtail, favorable interfere with or stop the immunopathologic process associated with circulating humoral antibody and/or immune complexes of the plasma. [Glassman, Rationale for Plasmapheresis, "Plasma Therapy" Vol. 1 No. 1, Page 13 (1979).]

A known method is to plasmapherese about 4 liters of blood by centrifugation or cross-flow filtration over a period of 2–4 hours. The plasma removed from the patient in this way is usually discarded and replaced by albumin and either physiological saline or Ringer's solution to make up the protein, electrolyte, and water balance. This is an expensive method. In another method the replacement of the removed plasma is accomplished by giving fresh or frozen pool plasma, and though less expensive, suffers from the risk of transmitting hepatitis virus to the patient. The method of the present invention (referred to as immunepheresis) overcomes these problems by selectively removing euglobulins or euglobulin antigen complexes causing or resulting from the disease and at the same time restoring the major portions of albumin, electrolyte (salt) and water and thus returning to the patient his or her own plasma (substantially depleted in Ig or Ig antigen complex) containing the proper protein, risk free from hepatitis since no additional albumin or donor plasma is required.

Antihemophilic factor (AHF) or antihemophilic globulin (Factor VIII, AHF or AHG) is one or the constituents involved in the coagulation of blood. A hereditary disorder or blood coagulation, hemophilia, results in profuse bleeding in joints, muscles or internal organs as a result or minor trauma. This disease appears to be due to a deficiency of a specific plasma protein AHF. Affected individuals frequently require therapy following minor accidents. In case surgery is required, clotting abnormality is corrected by fresh plasma transfusions or by injection of Factor VIII concentrate, the latter being preferred since it avoids hyperproteinemia and possible kidney dysfunction resulting from large volume transfusions.

Prior art methods for production of AHF consist for example, of taking pool-plasma, forming a cryoprecipitate, centrifuging the precipitate which mainly consists of a mixture of AHF and fibrinogen, removing fibrinogen and thereafter employing lyophilization to produce AHF concentrate. These methods suffer from the disadvantages of being long and cumbersome and of having the risk of transmitting hepatitis because of the pool-plasma source. Also the presence of fibrinogen as an impurity makes it difficult for the AHF concentrates to go into solution. In addition, due to an elapse of several days between donation and use there is a considerable loss of AHF activity. An AHF unit is defined as the activity present in 1 ml. of average normal pooled human plasma which is less than 1 hour old (100% AHF level). Thus after six hours the loss in activity in extra corporeal liquid plasma can be as great as 80%. A rapid method of processing AHF would prevent this loss of activity. The apparatus and methods of the present invention overcome these problems by being suited to an on-line real-time method. Therefore the recovery of AHF can be as high as 4 to 5 times that of the present, long elapsed time methods. The present invention is adaptable to a smaller pooled source. e.g. 2–3 hepatitis-free members of the hemophiliac's family can donate plasma and have the AHF recovered on site with a short time thereafter thus providing a hepatitis free AHF of very high activity. On-line methods of this invention can also be used to recover Factor VIII from donors during plasmapheresis.

The basic techniques employed in the present invention i.e., plasmapheresis, salting-out and dialysis when combined in a novel manner as described herein produces a synergism, i.e., it increases the usefulness of each step and the combination of steps in a previously unexpected manner and makes them extremely efficacious especially for in situ therapeutic use for plasmapheresis patients where removal of Ig's or their complexes is required.

The methods of the present invention will be described using plasma proteins as the preferred examples but the scope of this invention can also be applied to other biological fluids or proteins without limiting the scope of the invention. These methods for protein separation can serve as a very efficient tool in the hands of protein chemists.

THE INVENTION

The present invention relates to the separation of protein mixtures into protein fractions having intrinsically distinguishable compositions as determined by well known physical or chemical procedures. The invention involves the combination of plasmapheresis; the salting-out of proteins followed thereafter by dialysis for removal and/or make-up of the electrolytic balance of plasma. This procedure is useful when therapy requires the removal of immunoglobulins and their complexes and the return of essentially all (and only) the patient's own albumin. This avoids the risk of transmitting hepatitis and also accomplishes the therapy at a lower cost since albumin replacement is quite expensive.

After the removal from blood of formed elements (FE), the salting-out agent is added to the resulting plasma as a highly concentrated salt solution with constant stirring. The salt addition will result in the various proteins being precipitated out one-by-one as the ionic (salt) strength increases. The salting-out agents apparently operate by decreasing the activity of the water in the solvent mixture, thereby dehydrating the hydrophilic groups of the protein molecules thus resulting in the precipitation of proteins. The amount of salt added will depend upon the particular protein(s) to be removed. Thus for a 50–60% removal of the globulin fraction the addition of a salting-out agent such as $Na_2SO_4$ is made to bring the sodium sulfate normality of plasma to about 1–1.3. The turbidity resulting from the salting-out is thereafter removed for example as by filtration. The remaining supernatant is then dialyzed against a suitable buffer to remove the added $Na_2SO_4$ salt and then returned back to the patient after adding those previously removed blood cells or formed elements. Thus such a process combining plasmapheresis and salting-out followed by restoration of the normal electrolyte concentration is suited for therapeutic plasma exchange, obviating the necessity for using albumin or fresh or frozen, pool plasma. Removal of immuniglobulins by salting-out will be referred to herein as immunepheresis.

DETAILED DESCRIPTION

Dialysis is widely practiced in the biological field for the desalting or the make-up (addition) of electrolytes. Dialysis is a membrane separation process in which the driving force is a gradient in chemical potential e.g. a gradient in the concentration or activity of the solutes across a membrane separating two solutions. The membrane is permeable to water and low molcular weight solutes. Such solutes diffuse through the membrane until the concentration gradient is negligible across the membrane. Thus dialysis can be quite an efficient process in situations where high concentration gradients are involved. The main application of dialysis is in the kidney dialysis field where low molecular weight solutes, such as urea and certain salts, are removed. Such dialysis systems are well known and are fully described in U.S. Pat. Nos. 4,192,748, 4,191,646, 4,213,859, 3,960,730, and others. Its use however in conjunction with the salting-out of immunoglobulins and plasmapheresis is totally novel and not known in the prior art. The synergism resulting from combining these processes increases the efficacy of the combination especially when applied to therapeutic use of immunepheresis.

Figure 1:
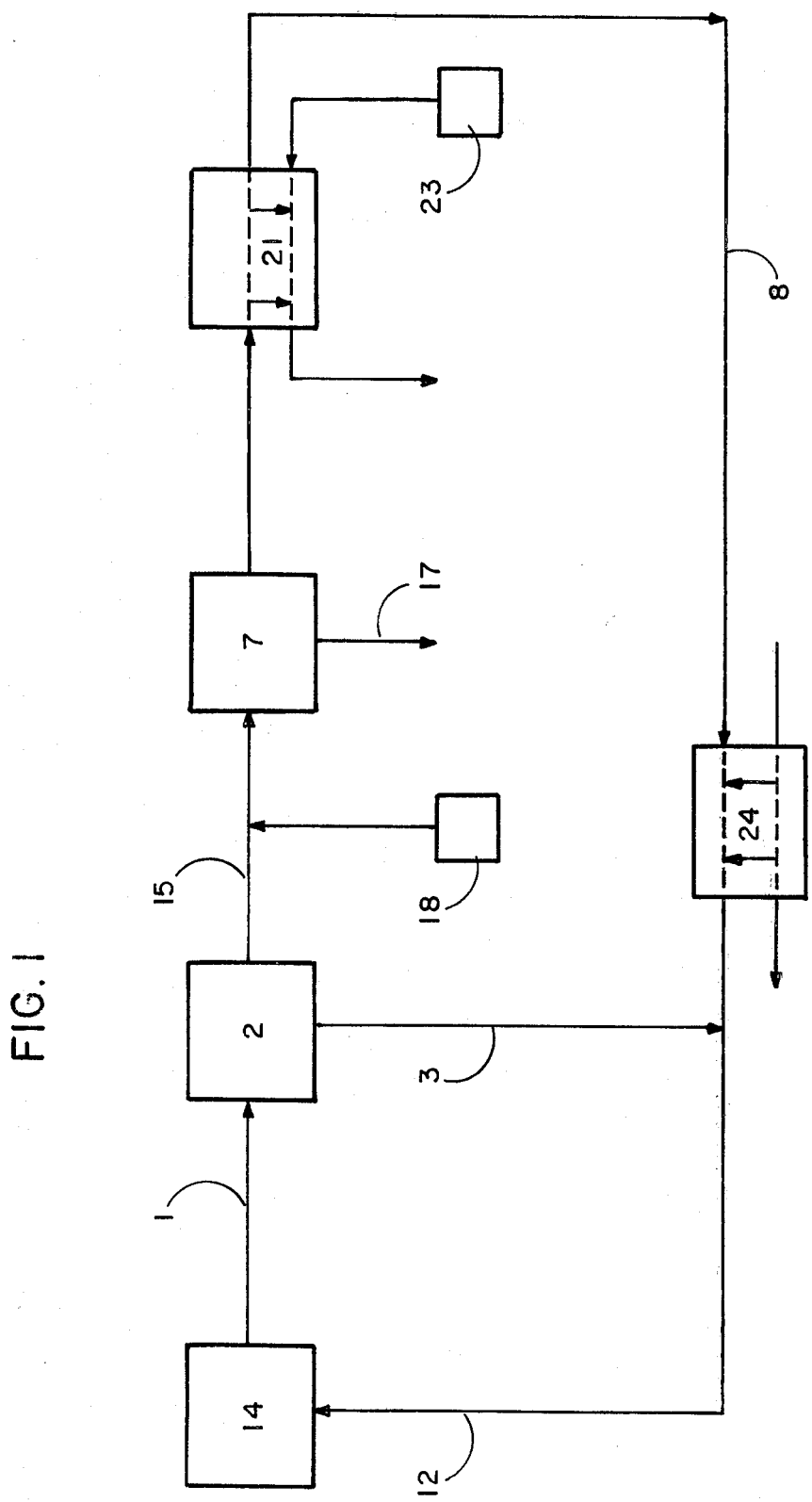

FIG. 1 shows the process of immunepheresis of this invention. In this drawing, the protein mixture illustrated is blood but the process could be applicable to other protein mixtures. An anticoagulant is first added to the patient's blood (1) and from the anticoagulated blood the formed elements (FE) consisting primarily of red cells, white cells and platelets are removed (3) by means of a membrane filter or a centrifuge (2) resulting in a clear plasma stream (15). A concentrated solution of a salting-out agent (18) such as sodium sulfate is directly added with mixing to the plasma. When about 50% IgG removal is desired, salt is added until the plasma becomes about 1.1–1.2 N in $Na_2SO_4$. If the aim is to remove a greater amount (%) of IgG and/or the removal of IgM and IgA, the amount of salt added should be higher. The following example shows this fractionation.

EXAMPLE I

Figure 2:
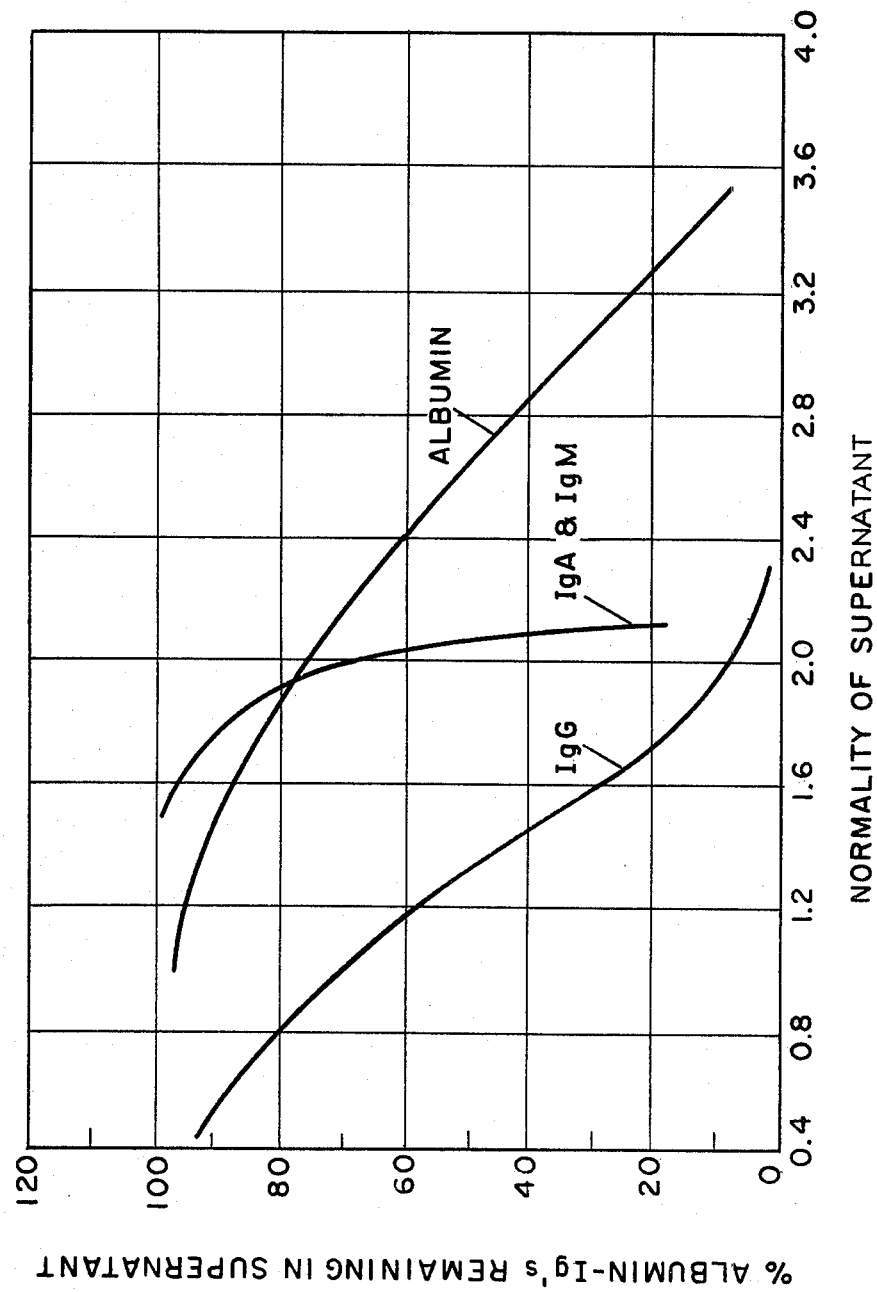

A 6 N $Na_2SO_4$ solution was gradually added with constant stirring to 300 ml. of plasma at a rate of about between 10–15 ml./min. Small samples of the plasma were withdrawn at various intervals and plasma protein and salt concentration analysis were performed. The results showing percentage of protein removal (i.e. albumin and Ig's) as a function of salt normality in the supernatant plasma is shown in FIG. 2. It will be noted that at a 2 normal salt concentration substantially all of the IgG is removed from the plasma accompanied by a 25% removal (loss) of albumin.

The turbidity (Ig's) resulting from the salt addition is removed (17) by a centrifuge or filter (7). This removal step may be combined with chilling (not shown) in order to facilitate faster removal of this turbidity. The addition of the salting-out agent is preferably done at the physiological temperature of 37° C. but it can also be done at room temperature or lower with suitable selection of the salting-out agent.

The supernatant (8) remaining after removal of the precipitated Ig's and their complexes is rich in albumin but contains a high concentration of salting-out agent which is removed by a dialysis apparatus (21). The albumin solution is dialyzed against a suitable buffer (23) e.g. PBS (0.1 N NaCl, 0.1 N $K_2HPO_4$). The dialysis step may consist of an initial dialysis (21) (for reducing the $Na_2SO_4$ to low levels) and a final dialysis (24) to make up the electrolyte balance for infusion. Since the objective of the initial dialysis is to remove the excess salt but retain albumin, the dialysis membrane such as cellulose can be chosen to give a high removal of the salting out agent. The salting-out agent may comprise a mixture of salts, e.g., $Na_2SO_4$ and NaCl as illustrated by the following example:

EXAMPLE II

Figure 3:
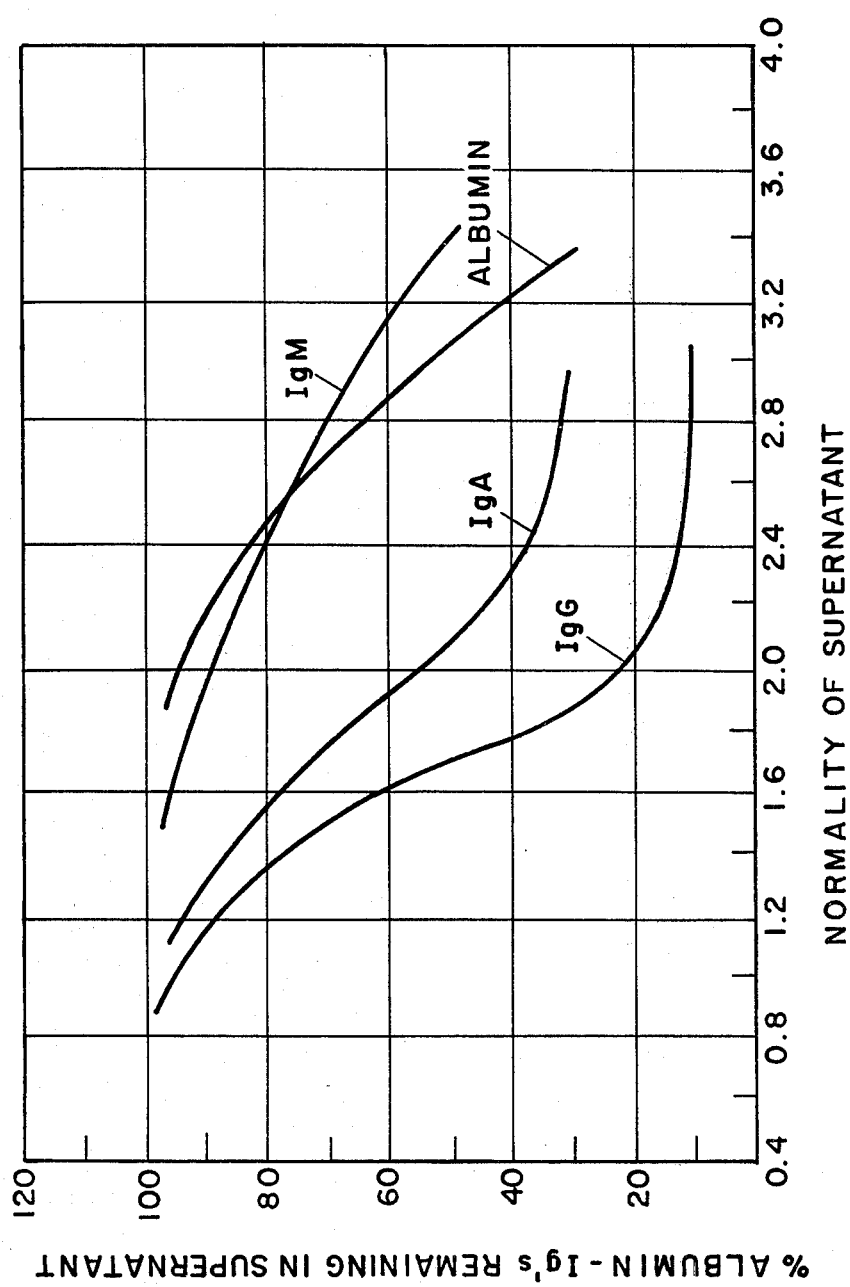

A salting-out agent comprising a mixture of 6 N $Na_2SO_4$ and 6 N NaCl was added to 300 ml. of plasma in the same manner employed in the previous example. The results of this protein fractionation curve is shown in FIG. 3. It will be noted that at a salt concentration in the supernatant of about 2.4 normal, about 90% removal of the IgG occurs with about a 15% removal (loss) of albumin. In comparing these results with that of example I it will be noted that a higher salt concentration is required to remove the Ig's where the salt mixture is employed although albumin loss appears to be less.

The choice of a salting-out agent will depend on the objective of retention or removal of a particular protein or set of proteins. Examples of other salting-out agents useful in the present invention are, for example, $(NH_4)_2SO_4$, $K_2SO_4$, sodium citrate, potassium acetate, $MgSO_4$, NaCl, etc. or their mixtures.

After removal of the salting out agents by dialysis (21) to an acceptable level, the desalted protein solution (8) (albumin mainly) is restored with the proper electrolyte by direct salt addition or by dialysis (24), mixed with the formed element (3) and then given back to the patient as restored blood (12).

Thus such a system as described above has the potential as an on-line method where a large enough dialysis area with a salt clearance membrane is provided. Alternatively it could be easily employed as an inexpensive off-line method also. Thus during the first plasmapheresis treatment, approximately 3.0 liters of the patient's plasma is replaced in the conventional way, i.e. by 1.5 liters of 5% albumin and 1.5 liters saline. During the second plasmapheresis treatment enough albumin is recovered from the 3.0 liters of plasma (obtained from the first plasmapheresis) by the method of this invention. This albumin from the first treatment is used to replace the second volume of plasma and thus each subsequent treatment uses the previously regenerated albumin rather than any additional albumin from outside. Being the patient's own albumin the treatment is free from risk of hepatitis.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent assemblies and methods.

The embodiments of this invention in which an exclusive property or privilege is claimed are defined as follows:

1. A process for separating an aqueous protein mixture into fractions having intrinsically distinguishable compositions comprising removing substantially all the turbidity therefrom, subsequently adding a salting-out agent thereto by passing said mixture into and out of a dialysis apparatus thereby increasing the ionic environment of the said mixture sufficiently to at least partially destabilize one or more proteins in said mixture, allowing said destabilized proteins to form turbidity, subsequently removing substantially all of said turbidity while maintaining the temperature of said mixture during the said separation in the range of between about 0°–40° C. and subsequently removing the salting-out agent by dialysis treatment.

* * * * *